US00PP08992P

United States Patent [19]

VandenBerg

[11] Patent Number: Plant 8,992

[45] Date of Patent: Nov. 29, 1994

[54] CHRYSANTHEMUM PLANT NAMED LISA

[75] Inventor: Cornelis P. VandenBerg, Salinas, Calif.

[73] Assignee: Yoder Brothers, Inc., Barberton, Ohio

[21] Appl. No.: 169,191

[22] Filed: Dec. 20, 1993

[51] Int. Cl.[5] ..... A01H 5/00

[52] U.S. Cl. ..... Plt./78

[58] Field of Search ..... Plt. 78, 82.2

*Primary Examiner*—Howard J. Locker

*Attorney, Agent, or Firm*—Foley & Lardner

[57] ABSTRACT

A Chrysanthemum plant named Lisa particularly characterized by its flat capitulum form; quilled to spooned decorative capitulum type; yellow ray floret color; diameter across face of capitulum of 51 to 60 mm when fully opened; branching pattern is spreading and prolific, with 8 to 9 breaks after pinch when grown outside under natural daylength in fall flowerings and 5 to 7 breaks when grown in 10 cm pots for spring flowerings; natural season flower date of August 16 to 24 when planting rooted cuttings on June 21 to 25 in Salinas, Calif., and September 20 to October 2 when planting rooted cuttings June 11 to June 18 in Hightstown, N.J.; flowering response of 44 to 51 days after rooting in no light/no shade programs in spring in Salinas, plant height of 28 to 36 cm when grown in fall under natural daylength with no growth regulators in New Jersey, and 15 to 23 cm when grown in 10 cm pots in spring with no growth regulator applications; and durable, uniform performance.

3 Drawing Sheets

The present invention comprises a new and distinct cultivar of Chrysanthemum, botanically known as *Dendranthema grandiflora,* and referred to by the cultivar name Lisa.

Lisa, identified as 9090 (87-342001), was originated from a cross made by Cornelis P. VandenBerg in a controlled breeding program in Salinas, Calif., in 1985.

The female parent of Lisa was an unnamed seedling identified as 3243 (79-M56002) and described as a quilled decorative garden mum with a yellow ray floret color. The female parent was discarded from all programs in October 1986.

The male parent of Lisa was an unnamed seedling, identified as 0292 (83-631002) and described as a yellow daisy garden mum. The male parent was discarded from all programs in October 1989.

Lisa was discovered and selected as one flowering plant within the progeny of the stated cross by Cornelis P. VandenBerg in October 1987, in a controlled environment in Salinas, Calif.

The first act of asexual reproduction of Lisa was accomplished when vegetative cuttings were taken from the initial selection in December 1987 in a controlled environment in Salinas, Calif., by technicians working under supervision of Cornelis P. VandenBerg.

Horticultural examination of controlled flowerings of successive plantings has shown that the unique combination of characteristics as herein disclosed for Lisa are firmly fixed and are retained through successive generations of asexual reproduction.

Lisa has not been observed under all possible environmental conditions. The phenotype may vary significantly with variations in environment such as temperature, light intensity and daylength, without, however, any variance in genotype.

The following observations, measurements and comparisons describe plants growth in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Lisa, which, in combiantion, distinguish this Chrysanthemum as a new and distinct cultivar:

1. Flat capitulum form.
2. Quilled to spooned decorative capitulum type.
3. Yellow ray floret color. A slight bronzing of the ray floret color in Salinas flowerings has been observed.
4. Diameter across face of capitulum of 51 to 60 mm when fully opened.
5. Branching pattern is spreading and prolific, with 8 to 9 breaks after pinch when grown outside under natural daylength in fall flowerings and 5 to 7 breaks when grown in 10 cm pots for spring flowerings.
6. Natural season flower date of August 16 to 24 when planting rooted cuttings on June 21 to 25 in Salinas, Calif., and September 20 to October 2 when planting rooted cuttings June 11 to June 18 in Hightstown, N.J.
7. Flowering response of 44 to 51 days after rooting in no light/no shade programs in spring in Salinas.
8. Plant height of 28 to 36 cm when grown in fall under natural daylength with no growth regulators in New Jersey, and 15 to 23 cm when grown in 10 cm pots in spring with no growth regulator applications.
9. Under very high summer temperatures in Florida foliar flecks might appear on the leaves of the stock plants. These are small grey spots on the foliage, which will not develop under the cooler temperatures in the Northeastern and Western United States during the flowering periods.
10. Durable, uniform performance.

The accompanying photographic drawings show typical inflorescence and leaf characteristics of Lisa, with the colors being as nearly true as possible with illustrations of this type.

Sheet 1 is a color photograph of Lisa grown as a pinched garden mum under natural season outside conditions in Salinas, Calif. Plants were grown outside and dug and transplanted into 15 cm bulb pans at flowering time for photography purposes.

Sheet 2 is a black and white photograph of three views of the inflorescence of Lisa.

Sheet 3 is a black and white photograph showing the upper and under sides of the leaves of Lisa at 3 stages of development (mature, intermediate and immature). In sheets 2 and 3 a measuring tape in centimeters has been added.

Of the commercial cultivars known to the inventor, the most similar in comparison to Lisa is the cultivar identified as Jessica, disclosed in U.S. Plant Pat. No. 7,587. Reference is made to attached Chart A, which compares certain characteristics of Lisa to the same characteristics of Jessica.

Similar traits are ray floret color, capitulum form, and branching pattern. The diameter of capitulum and the plant height of Lisa and Jessica are in the same range. Lisa has a quilled to spooned capitulum type, while Jessica is described as having a decorative capitulum type. When compared with Jessica, Lisa has a later natural season flower date and a slower controlled response than Jessica.

In the following description, color references are made to The Royal Horticultural Society Colour Chart. The color values were determined on plant material grown as a pinched garden mum grown outdoors in Salinas, Calif. on Aug. 16, 1993.

Classification:

*Botanical.*—*Dendranthema grandiflora* cv Lisa.

*Commercial.*—Flat quilled to spooned decorative spray pot mum and garden mum.

INFLORESCENCE

A. Capitulum:

*Form.*—Flat.

*Type.*—Quilled to spoon decorative.

*Diameter across face.*—51 to 60 mm when fully opened.

B. Corolla of ray florets:

*Color (general tonality from a distance of three meters).*—Yellow.

*Color (upper surface).*—12A to 12B.

*Color (under surface).*—12A to 12B. Underside and tips of immature ray florets and buds very slightly tinged with 167D.

*Shape.*—See photograph.

C. Corolla of disc florets:

*Color (mature).*—14A.

*Color (immature).*—14A tinged with 144C.

D. Reproductive organs:

*Androecium.*—Present on disc florets only; scant pollen.

*Gynoecium.*—Present on both ray and disc florets.

PLANT

A. General appearance:

*Height.*—28 to 36 cm when grown in fall under natural daylength with no growth regulators in New Jersey, and 15 to 23 cm when grown in 10 cm pots in spring with no growth regulator applications.

*Branching pattern.*—Spreading and prolific, with 8 to 9 breaks after pinch when grown outside under natural daylength in fall flowerings and 5 to 7 breaks when grown in 10 cm pots for spring flowerings.

B. Foliage:

*Color (upper surface).*—147A.

*Color (under surface).*—147B.

*Shape.*—See photograph.

CHART A

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

| | LISA | JESSICA |
|---|---|---|
| Ray floret color | Yellow | Yellow |
| Capitulum form and type | Flat quilled to spooned decorative | Flat decorative |
| Diameter across face of capitulum | 51 to 60 mm | 50 to 63 mm |
| Branching pattern | Spreading and prolific | Spreading and prolific |
| Nat. season flower date: | | |
| in Salinas, CA | Aug 16 to 24 | Aug 8 to 22 |
| in Hightstown, NJ | Sep 20 to Oct 2 | Sep 8 to 21 |
| Controlled response | 44 to 51 days | 41 to 47 days |
| Plant height: | | |
| in natural season fall | 28 to 36 cm | 23 to 36 cm |
| in 10 cm pots spring | 15 to 23 cm | 15 cm |

I claim:

1. A new and distinct Chrysanthemum plant named Lisa, as described and illustrated.

* * * * *

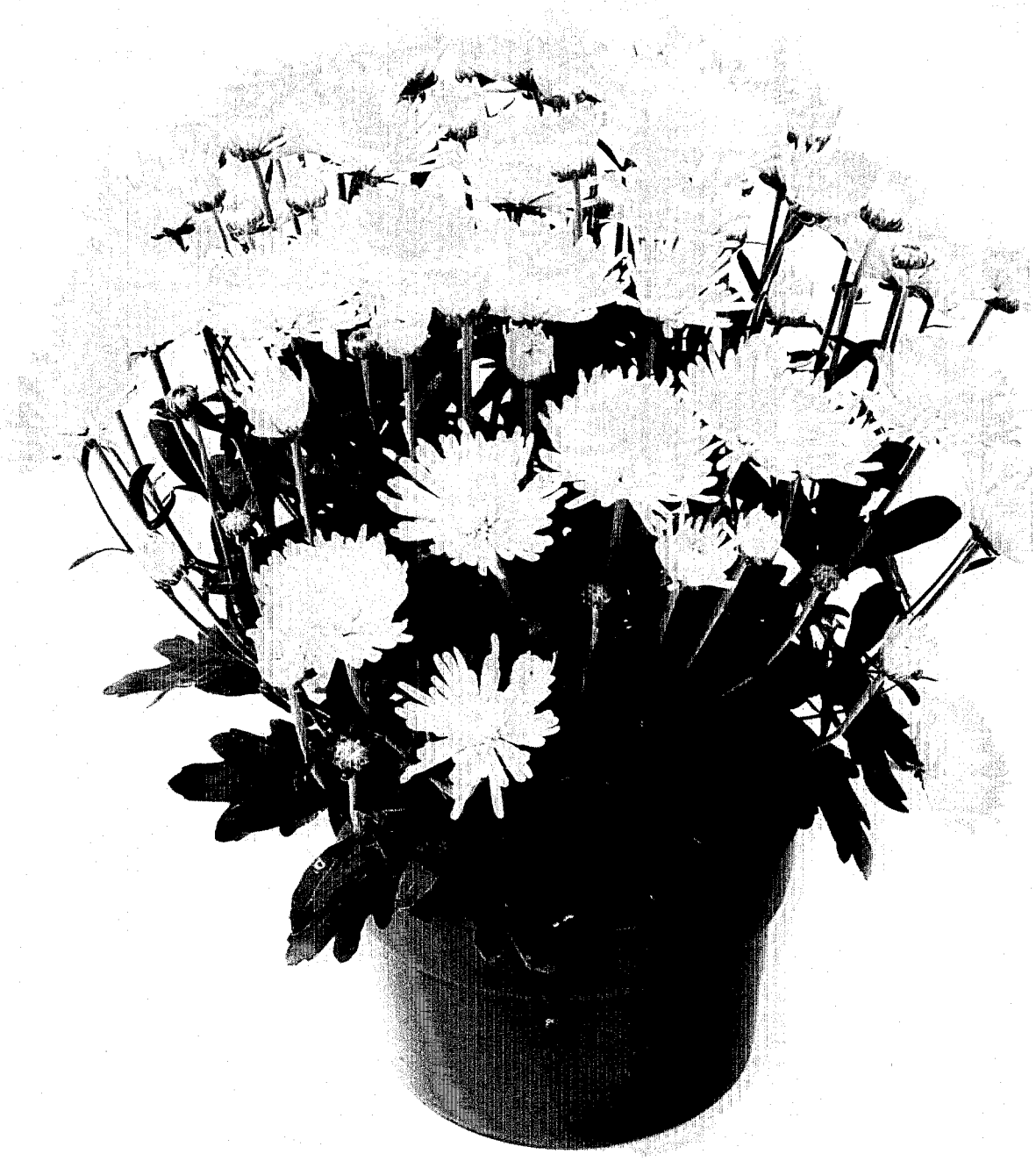

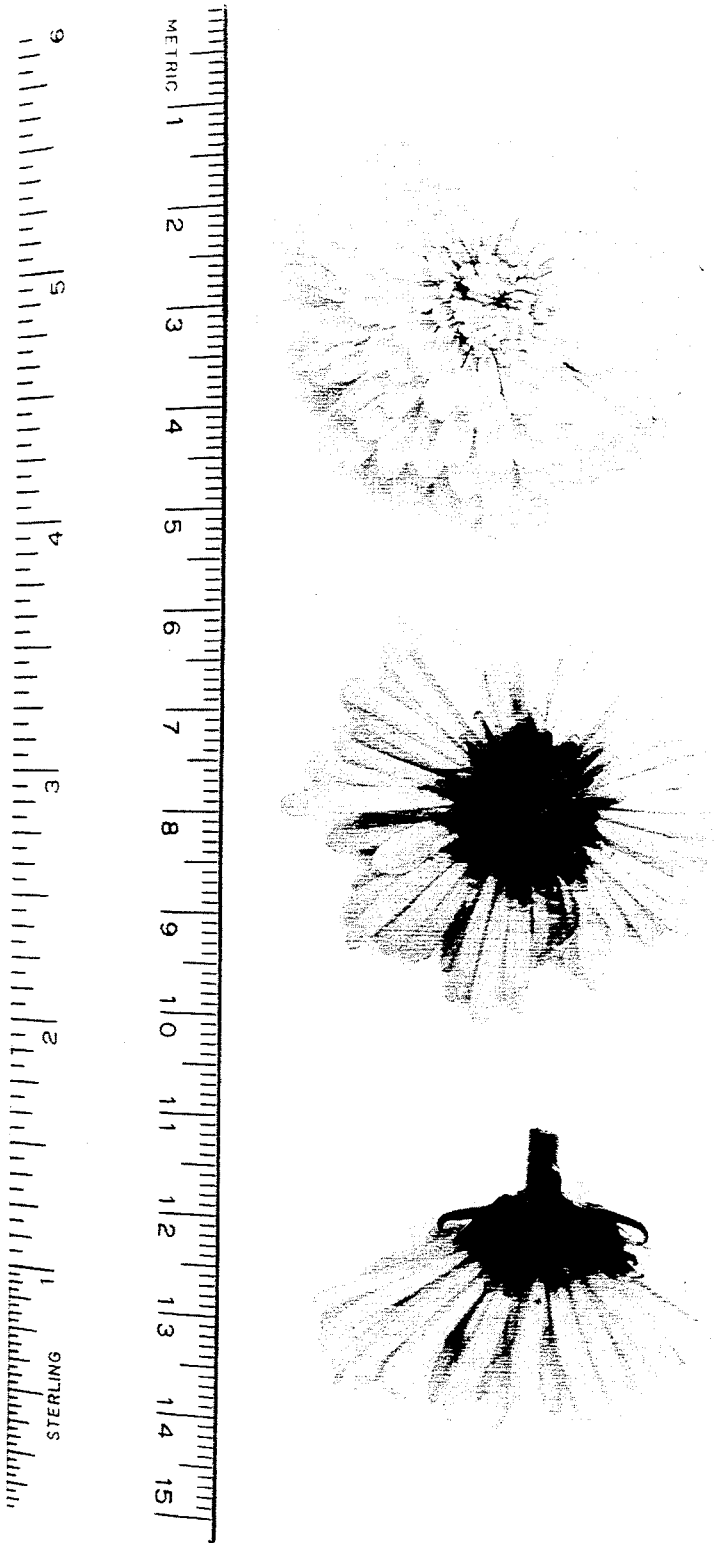
METRIC
STERLING

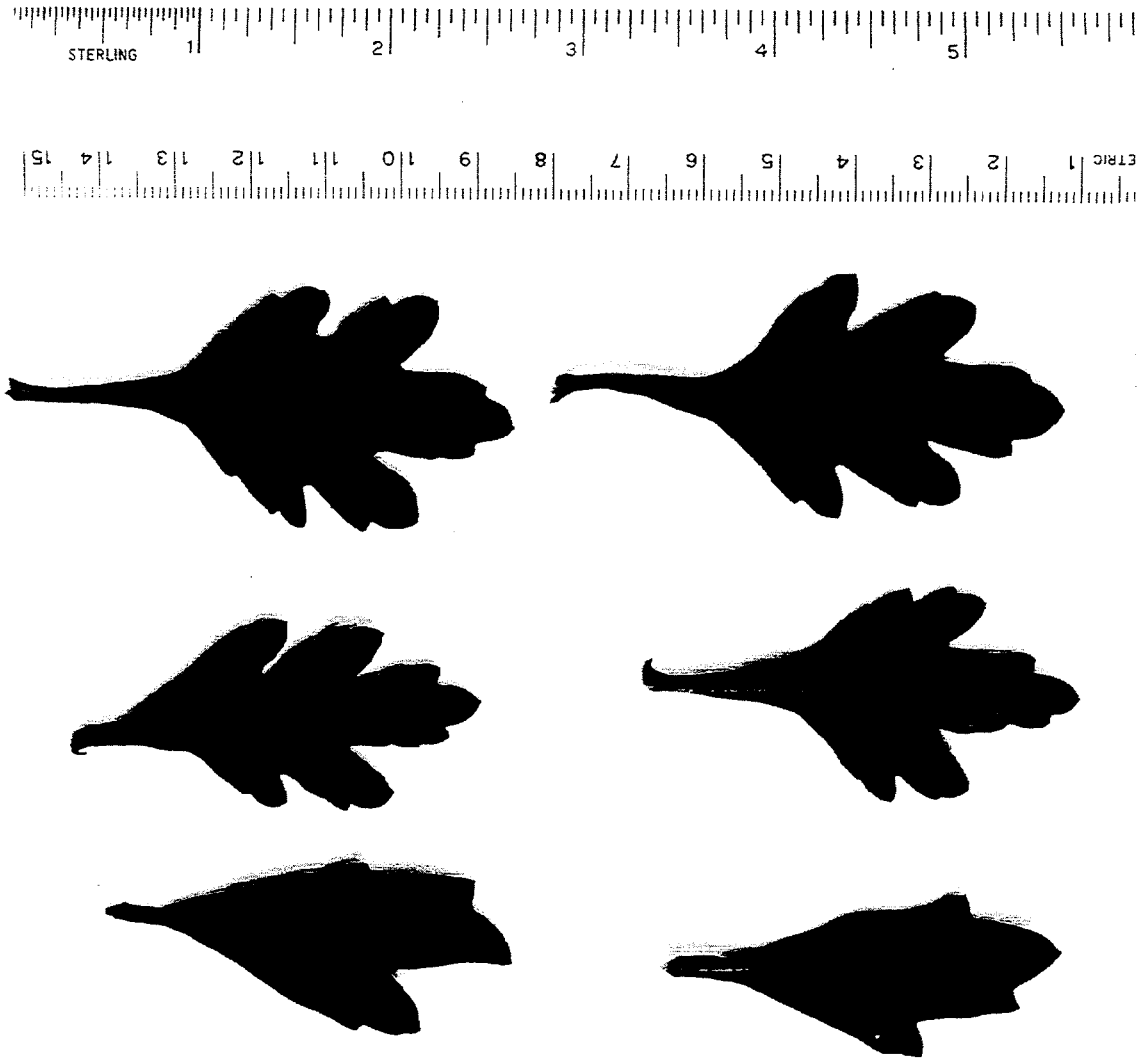
STERLING
1
2
3
4
5
ETRIC
1
2
3
4
5
6
7
8
9
10
11
12
13
14
15